(12) United States Patent
Na

(10) Patent No.: US 11,406,444 B2
(45) Date of Patent: *Aug. 9, 2022

(54) ELECTRICALLY BASED MEDICAL TREATMENT DEVICE AND METHOD

(71) Applicant: Jongju Na, Songpa-Gu (KR)

(72) Inventor: Jongju Na, Songpa-Gu (KR)

(\*) Notice: Subject to any disclaimer, the term of this patent is extended or adjusted under 35 U.S.C. 154(b) by 40 days.

This patent is subject to a terminal disclaimer.

(21) Appl. No.: 17/061,523

(22) Filed: Oct. 1, 2020

(65) Prior Publication Data

US 2021/0015546 A1    Jan. 21, 2021

Related U.S. Application Data

(63) Continuation of application No. 16/111,616, filed on Aug. 24, 2018, now Pat. No. 10,799,286, which is a (Continued)

(30) Foreign Application Priority Data

Jun. 14, 2011  (KR) .................. 10-2011-0057691
Jun. 14, 2011  (KR) .................. 10-2011-0057692

(51) Int. Cl.
*A61B 18/14*    (2006.01)
*A61H 39/00*    (2006.01)
(Continued)

(52) U.S. Cl.
CPC ....... *A61B 18/1477* (2013.01); *A61H 39/002* (2013.01); *A61H 39/086* (2013.01); *A61N 1/0502* (2013.01); *A61N 1/06* (2013.01); *A61N 1/328* (2013.01); *A61B 2018/0047* (2013.01); *A61B 2018/0072* (2013.01); *A61B 2018/00452* (2013.01); *A61B 2018/00589* (2013.01); *A61B 2018/00625* (2013.01); (Continued)

(58) Field of Classification Search
CPC ....... A61N 1/05; A61N 1/0534; A61N 1/0551
See application file for complete search history.

(56) References Cited

U.S. PATENT DOCUMENTS 4,180,079 A   12/1979  Wing
5,465,593 A   11/1995  Takasu
(Continued)

FOREIGN PATENT DOCUMENTS

JP    2009-506873 A    2/2009
KR  10-2006-0027194 A  3/2006
(Continued)

OTHER PUBLICATIONS

Translated Written Opinion of the International Searching Authority For International application No. PCT/KR2012/001335 dated Sep. 28, 2012 (7 pages).
(Continued)

*Primary Examiner* — Amanda K Hulbert
*Assistant Examiner* — Philip C Edwards
(74) *Attorney, Agent, or Firm* — Merle W. Richman, Esq.

(57) ABSTRACT

Embodiments of medical treatment including skin treatment using electrical energy, especially with the primary purpose for skin treatment for aesthetics are described generally herein. Other embodiments may be described and claimed.

18 Claims, 7 Drawing Sheets

Related U.S. Application Data continuation of application No. 15/202,511, filed on Jul. 5, 2016, now Pat. No. 10,058,379, which is a continuation of application No. 14/006,930, filed as application No. PCT/KR2012/004695 on Jun. 14, 2012, now Pat. No. 9,480,836.

(51) Int. Cl.

| | | |
|---|---|---|
| *A61H 39/08* | (2006.01) | |
| *A61N 1/06* | (2006.01) | |
| *A61N 1/32* | (2006.01) | |
| *A61N 1/05* | (2006.01) | |
| *A61B 18/00* | (2006.01) | |
| *A61B 18/12* | (2006.01) | |

(52) U.S. Cl.
CPC .......... *A61B 2018/00726* (2013.01); *A61B 2018/00732* (2013.01); *A61B 2018/00738* (2013.01); *A61B 2018/00767* (2013.01); *A61B 2018/126* (2013.01); *A61B 2018/143* (2013.01); *A61B 2018/1475* (2013.01)

(56) References Cited

U.S. PATENT DOCUMENTS

| | | | |
|---|---|---|---|
| 5,546,954 | A | 8/1996 | Yamada |
| 6,931,277 | B1 | 8/2005 | Yuhakov et al. |
| 6,890,319 | B1 | 10/2005 | Crocker |
| 7,133,717 | B2 | 11/2006 | Coston et al. |
| 7,618,429 | B2 | 11/2009 | Mulholland |
| 7,824,394 | B2 | 11/2010 | Manstein |
| 8,979,912 | B2 | 3/2015 | Na et al. |
| 9,320,536 | B2 | 4/2016 | Na |
| 2004/0058882 | A1 | 3/2004 | Eriksson et al. |
| 2005/0222565 | A1* | 10/2005 | Manstein .............. A61M 5/158 606/41 |
| 2006/0293725 | A1 | 12/2006 | Rubinsky et al. |
| 2007/0038181 | A1 | 2/2007 | Melamud |
| 2007/0073217 | A1 | 3/2007 | James |
| 2007/0142885 | A1 | 6/2007 | Hantash et al. |
| 2007/0231255 | A1 | 10/2007 | Barolet et al. |
| 2007/0232962 | A1 | 10/2007 | Zumeris et al. |
| 2007/0276318 | A1 | 11/2007 | Henley |
| 2008/0014627 | A1 | 1/2008 | Merchant et al. |
| 2008/0082090 | A1 | 4/2008 | Manstein |
| 2008/0091182 | A1 | 4/2008 | Mehta |
| 2008/0114298 | A1 | 5/2008 | Cantor et al. |
| 2008/0269666 | A1 | 10/2008 | Wang et al. |
| 2008/0281389 | A1 | 11/2008 | Knopp |
| 2009/0312691 | A1 | 12/2009 | Kim et al. |
| 2011/0046615 | A1 | 2/2011 | Manstein |
| 2012/0138335 | A1* | 6/2012 | Tathireddy .......... A61N 1/0529 174/250 |

FOREIGN PATENT DOCUMENTS

| | | |
|---|---|---|
| KR | 10-2010-001828 A | 2/2010 |
| KR | 10-2010-0055292 A | 5/2010 |
| KR | 10-2011-0002210 A | 1/2011 |
| WO | 00/74763 A2 | 12/2000 |
| WO | 2005/058407 A1 | 6/2005 |
| WO | 2005/096979 A1 | 10/2005 |
| WO | 2008/004781 A1 | 10/2008 |

OTHER PUBLICATIONS

Translated International Search report for International application No. PCT/KR2012/004695 dated Sep. 28, 2012 (3 pages) PCT/KR2012/001335 dated Sep. 28, 2012 (3 pages).
Translated Written Opinion of the International Searching Authority For International application No. PCT/KR2012/004695 dated Jan. 2, 2013 (7 pages).
Translated International Search report for International application No. PCT/KR2012/004695 dated Dec. 31, 2012 (2 pages).

\* cited by examiner

ELECTRICALLY BASED MEDICAL TREATMENT DEVICE AND METHOD

CROSS REFERENCE TO RELATED APPLICATIONS

The present application is a continuation of U.S. application Ser. No. 16/111,616, entitled "ELECTRICALLY BASED MEDICAL TREATMENT DEVICE AND METHOD", filed on Aug. 24, 2018, which is a continuation of U.S. application Ser. No. 15/202,511, entitled "ELECTRICALLY BASED MEDICAL TREATMENT DEVICE AND METHOD", filed on Jul. 5, 2016, now U.S. Pat. No. 10,058,379, which is a continuation of U.S. application Ser. No. 14/006,930, entitled "SKIN TREATMENT APPARATUS AND METHOD", filed on Jun. 23, 2013 now U.S. Pat. No. 9,480,836, which is a Rule 371 national stage entry of PCT Application Number PCT/KR2012/004695, entitled "APPARATUS AND METHOD FOR IMPROVING SKIN USING A NA-EFFECT OR NA PLUS-EFFECT", filed on Jun. 14, 2012, which claims the benefit of priority to Republic of Korea Application Number 10-2011-0057691, entitled" APPARATUS AND METHOD FOR IMPROVING SKIN USING A NA-EFFECT OR NA PLUS-EFFECT," filed on Jun. 14, 2011, and Republic of Korea Application Number 10-2011-0057692, entitled "APPARATUS AND METHOD FOR IMPROVING SKIN USING A NA-EFFECT OR NA PLUS-EFFECT," filed on Jun. 14, 2011, the entirety of each is incorporated by reference.

TECHNICAL FIELD

This invention is for medical treatment including skin treatment using electrical energy, especially with the primary purpose for skin treatment for aesthetics, and in some cases, can be used as a direct instrument or supplement for skin cosmetic surgery.
In detail, this invention is to provide skin treatment using method and device using high frequency, which minimizes skin aging by directly stimulating dermis between epidermis and subcutaneous layer.

BACKGROUND INFORMATION

Generally, skin is the largest protective organ that covers the entire body and maintains homeostasis on surface of the body with three layers consisting of epidermis, dermis, and subcutaneous layer.

Dermis is the layer beneath epidermis, directly connected to a basal layer. Skin is made up of dermis that includes protein, glycoside, glycosaminoglycan, mineral, and inorganic salt in gelatinous form. In Dermis there are two layers: papillary and reticular layer. The Papillary layer includes of capillaries and lymphatics. Capillaries provide nutrition to skin and circulate blood. Lymphatics carry lymph. The Reticular layer includes collagen, elastin and a substrate. Collagen is a fiber related to skin wrinkle, elastin is an elastic fiber that gives elasticity to skin, and the substrate is mostly made of water. The Subcutaneous layer lies below dermis, contains plenty of fat, and attaches the skin to underlying muscle and bone.

One of the most popular treatments to prevent skin aging is massaging with a nutritious substance. Although this type of skin treatment provides nutrition to epidermis and may make skin glow, it does not last for long and rarely shows improvement instantaneously.

Another treatment uses a syringe to inject serum into the skin, but this treatment method is costly and causes side effects based on individual skin characteristics that result adversely affecting the skin.

A further treatment delivers high frequency energy indirectly to the dermis via the skin surface. Even with a high energy signal, this treatment does not effectively transmit high frequency energy to the dermis via the skin surface. Also, this treatment is costly because patients may need to receive multiple treatments to obtain measurable results.

Korean patent 2000-0058346 describes a device to reduce skin wrinkles by verifying wrinkle thickness, length and shape and setting pulse, time, elevation current and wattage to magnify the cell tissue. Via a hand piece, the needle length may be selected based on the length and depth of wrinkle to be reduced. The device uses a single needle that may not be sufficient for treatment. Korean patent 10-2009-23494 describes employing high frequency to treat skin. In detail, it attempts to revitalize cell tissue and maintain elasticity in skin, and minimizing skin aging by directly delivering high frequency energy into skin dermis (between epidermis and subcutaneous layer). The skin treatment device includes a pair of electrodes in a main body that deliver high frequency energy into the dermis reticular layer. This treatment method may include side effects, not limited to burning both epidermis and dermis between the needles, which may form a scar. Another problem of the treatment is maintaining finite control.

To limit epidermis burning the needles may be insulated except at the tip portion. Insulated needles may cause bigger penetration marks, pain and possible allergic reactions in patients. The needle insulation may also fail or come off due to repeated penetration resulting in heating of unintended areas. In addition, the device may generate a high temperature around needle tip and increase the possibility of dermis burning since the needle surface area is reduced by the insulation.

Another device uses a monopole configuration with a single electrode and a ground on another body location. Such a configuration may require large voltages to conduct enough energy to generate desired heat. The high voltage conduction may impact unintended body parts including the heart.

SUMMARY OF THE INVENTION

The present invention is a method and apparatus that provides electric stimulation directly to a body region including the dermis via needles. This method revitalizes and regenerates the body region including collagen by wounding the dermis.

As noted, dermis is composed of protein called collagen. Collagen is a triple helical structure including fibroblasts and polypeptides. When collagen tissue is heated, a physical transformation of protein matrix part occurs at a shrinkage temperature. Soft tissue remodeling is a transformation and phenomenon that happens at cellular and molecular level when the triple helical binding is disassembled by partial denaturalization of collagen due to shrinkage caused by artificial heat, resulting in destruction of molecular bindings of the protein matrix. When the cell shrinkage occurs, collagen is present on lower cell part and supports the protein matrix within the resulting tightened soft tissue. The initial deposition and subsequent remodeling of scar matrix may offer a way to aesthetically modify the shape and consistency of soft tissue. Soft tissue remodeling may appear immediately compared to the shrinkage that results from the movement of fibroblast cell or natural healing. Ultimately, a treatment for improving skin or reducing wrinkles may apply various energy sources to selected areas to solidify the tissue.

When energy is applied to dermis, the effect on the dermis may differ based on the amount of energy applied and the effect is generally divided into three phenomena: carbonization, vaporization, and coagulation. The present invention improves skin condition by primarily using coagulation. The three phenomena: carbonization, vaporization, and coagulation can also be expressed as "to burn", "to apply heat", "to raise temperature", although none of these phrases are exact. The invention may configured "to raise temperature" by applying energy to achieve coagulation.

In the present invention the term "to raise temperature" is used synonymously with "applying energy to achieve coagulation" where applying electrically energy to the body region may effectively raise the body region temperature. The present invention was created to resolve above mentioned problems.

An embodiment of the present invention includes a skin improvement device and method is to resolve above mentioned problems. The present invention is a byproduct of newly discovered effects. A first embodiment is shown in FIG. 5. Other embodiments are shown FIGS. 7, 8 and 9B. Several embodiments of the present invention may employ non insulated needles, especially in areas where the needles come in contact with dermis.

In an embodiment heated areas may be different from other electrodes employing systems. In the present invention the temperature may be raised and the heat may be concentrated at an area in dermis by the needle(s) to cause coagulation. The heat generated by the present invention may minimally affect the adjacent epidermis area. Also, the heated area around the needle end tips may be oval or tear shaped as shown in FIG. 5. In an embodiment heat may not be concentrated between needles. In an embodiment, the heated area may be around each needle.

In an embodiment, the temperature is raised about the tip of each needle, not between needles. The method of the present invention may control electrical factors or distance between needles to control the energy field applied between needles. A method of the present invention may enable users to control the number of treatments in target areas by controlling the dissipated energy in needles.

In an embodiment, higher temperatures may be concentrated in dermis, not epidermis, enabling the use of non-insulated needles. The present invention may have a definite advantage over the systems that employ insulated needles. An embodiment of the present invention may not require insulated needles except for special cases. In some treatment cases, an embodiment of the present invention may employ insulating needles in an area where it comes in contact with epidermis, but insulation is not required.

An embodiment of the present invention may employ bipolar needles, alternating current (AC) signals, and high frequency signals. In an embodiment the distance between electrodes or needles may be important because if the distance between electrodes is too close, heated areas about each needle tip may overlap. However, in another embodiment a close distance between needles may not be critical.

As noted the present invention may use non-insulated needles. Other embodiments may use insulated needles but may, decrease the effectiveness of treatments employing insulated needles. Because the needles are stimulated via opposite polarity, AC signals, each needle may independently form an energy field about its tip, where the energy field may raise the temperature of adjacent tissue as a function of the tissue anatomy. Thus, each needle of the plurality of needles may as if independently stimulated and grounded from the other of the plurality of needles.

In an embodiment employed needles polarities may form a net or checked shape when viewed from needle tips. In an embodiment, four or more needles may be employed. In an embodiment where the needles form a rectangular plane, four or more needles may be used on each quadrant.

In an embodiment adjacent or neighboring needles may be configured to have opposite polarities (+) and (−) such as shown in FIG. 6.

Embodiments of the present invention may resolve problems of existing technologies.

A serious side effect of some existing technologies, systems, or treatments is overheating or burning of both dermis and epidermis located between needles, which may cause permanent skin damage. An embodiment of the present invention may prevent or limit overheating between needles.

As noted embodiments of the present invention may generate an oval or tear shaped, heated area in dermis about each needle tip. Embodiments of the present invention may minimally raise temperature epidermis as shown in FIG. 5. Method of the present invention may control electrical factors or distance between needles to control temperature between needles.

Existing technology may create scars created in overheated or burned epidermis. Further damage may be caused by trying to treat the scars. Embodiment of the present invention attempt to prevent overheating or burning of epidermis. Embodiments of the present invention may not use insulation as insulation may reduce effectiveness. Further, insulted needles may need to be thicker, causing more patient pain and leaving insertion marks. Further insulation deposited from needles may cause serious side effects.

BRIEF EXPLANATIONS OF THE DRAWINGS

DETAILED DESCRIPTION

The following is to explain an embodiment of this invention in detail.

Table of References

| Number | Description |
| --- | --- |
| 100: | fixture holding needles |
| 200: | skin |
| 201: | epidermis |
| 202: | dermis |
| 300: | pin/needle/electrode |
| 301: | needle area penetrating skin |
| 302: | end of needle area penetrating into dermis |
| 400: | patient's hand receiving treatment using monopole method |
| 500, 600: | electrical wire |
| 700: | insulated area of needle |
| 901: | area where the temperature is raised when using monopole electrode |
| 902: | area where the temperature is raised when using non-insulated bipolar needles |
| 903: | area where the temperature is raised using insulated needles with non-insulated tips |
| 909, 919, 929: | area where the temperature is raised using non-insulated needles. |
| 939, 949: | area where the temperature is raised using partially insulated needles in epidermis |

Figure 1:
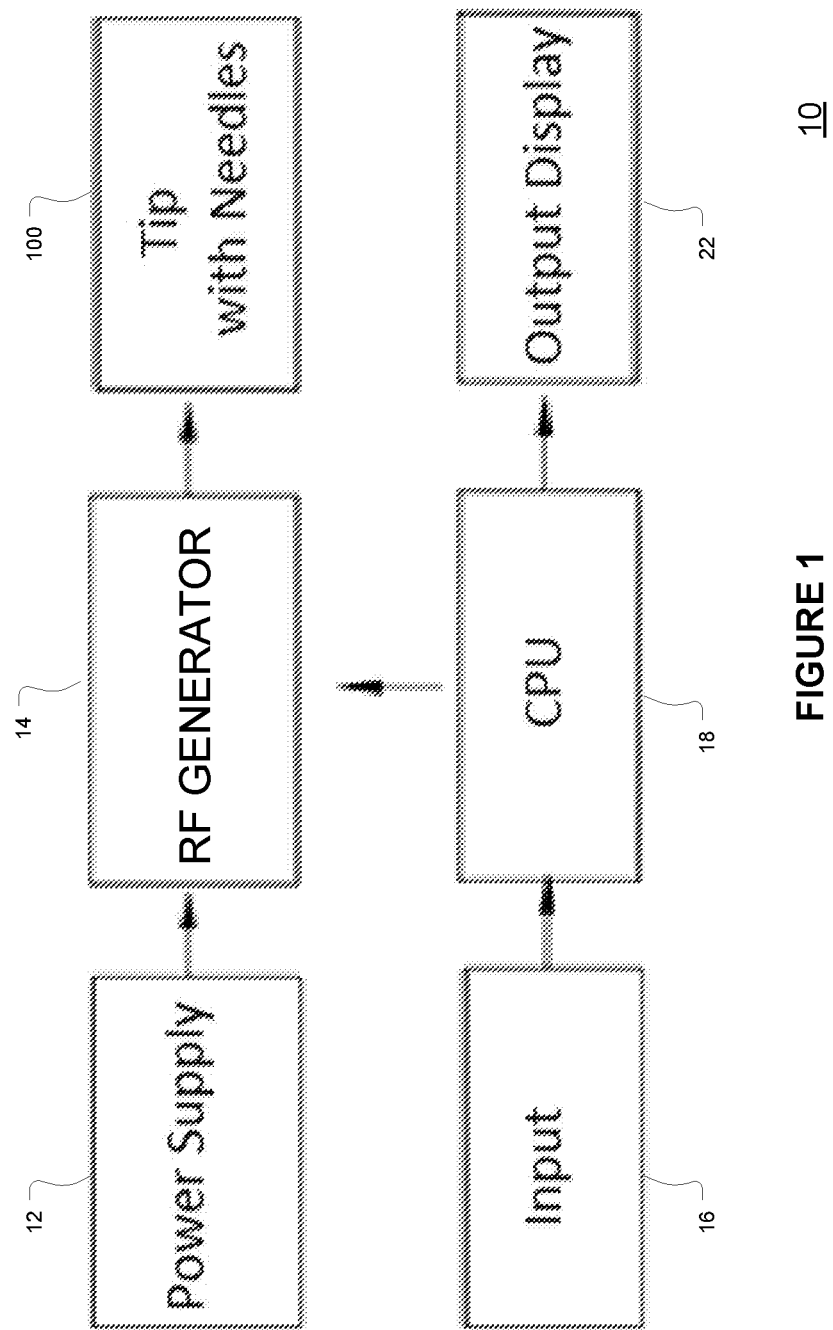
FIG. 1 is a block diagram of an apparatus according to an embodiment of the present invention.

This invention pursues multiple embodiments, where the embodiments may be related. Technological components of various embodiments may be similar. Embodiments may vary based on voltage, current, application time, needle thickness, resistance, AC frequency, high frequency, conductivity, and needle penetration depth. FIG. 1 is a block diagram a system 10 according to various embodiments. As shown in FIG. 1, the system 10 may include a power supply 12, an RF generator 14, a user input 16, a central processing unit 18, a user detectable output display 22, and a device (tip) 100 with a plurality of needles 300. The power supply 12 may provide required energy to the radio frequency (RF) generator 14. A user input device 16 may enable a user to set several parameters that control the energy field 909 generated about needles 300 in the tip or device 100 including the voltage, current, and frequency applied to the needles 300, the on time and off time of the RF signal during the cycles, the deployed depth of the needles (to treat a body region including epidermis, dermis, and subcutaneous sections of skin). The input device may be any device enabling a user to select various parameters including a keyboard, touch screen, or other user input device.

The system 10 output device 22 may be any user detectable output device including a user readable screen, light(s), and audio generation devices. The CPU 18 may receive the user selected parameters for the device 100 operation and control the operation of the RF generator 14 based on the user selected parameters. The CPU 18 may also provide a signal to generate an output signal displayable by the output device 22, the output signal indicating the operational state of the system 100 according to various embodiments. The RF generator 14 may generate signal or signal(s) having a desired voltage, current, energy, resistance, RF frequency, on cycle, off cycle, and other parameters according to various embodiments.

Figure 2:
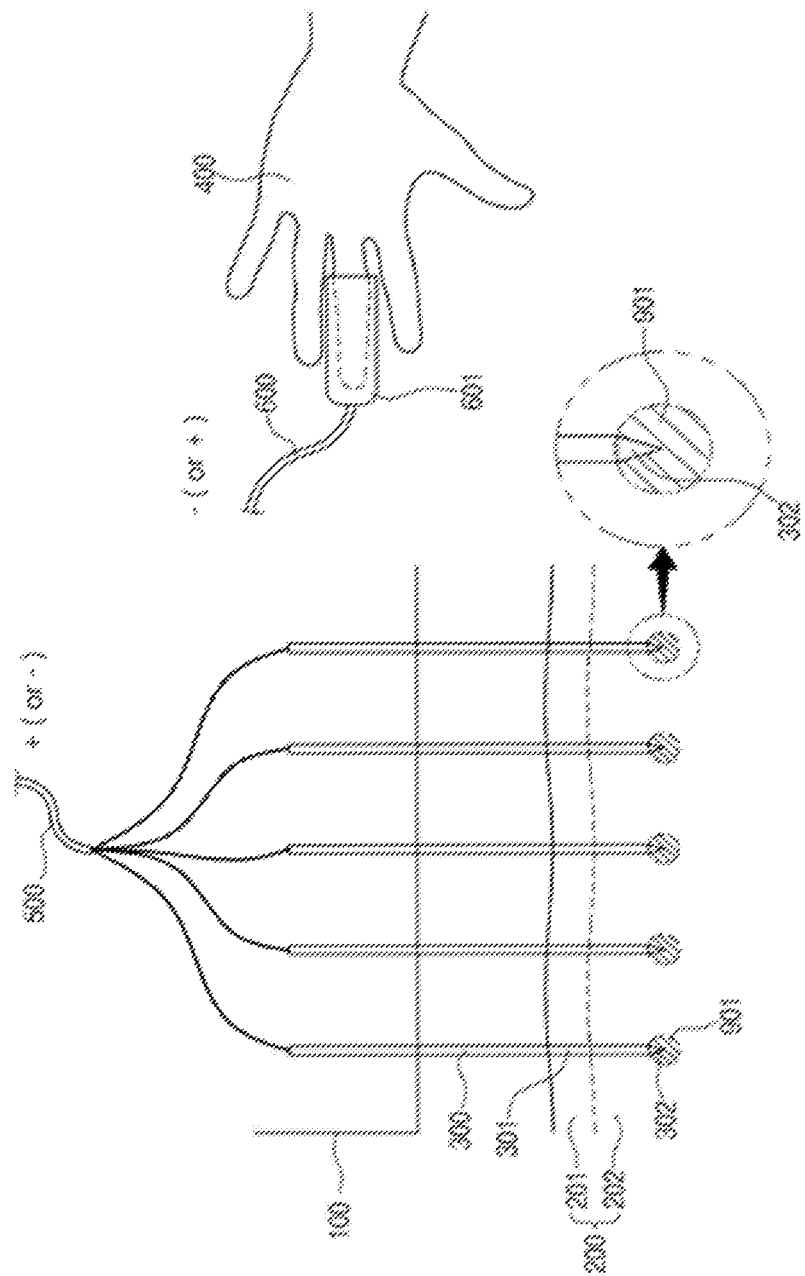
FIG. 2 is a simplified diagram of treatment architecture using monopole needles according to an embodiment of the present invention.
Figure 4:
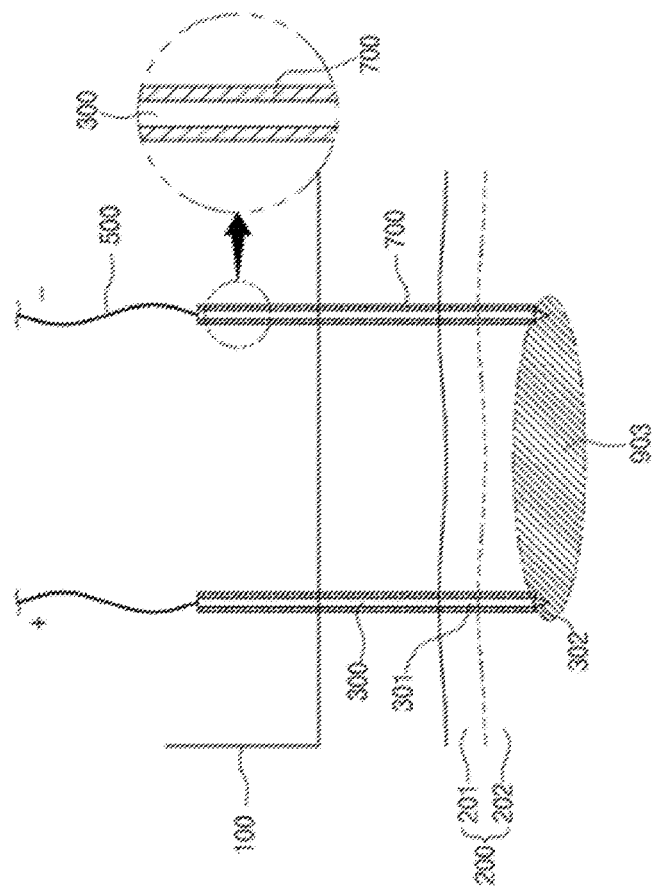
FIG. 4 is a simplified diagram of treatment architecture using bipolar needles that are insulated except at the needle tip according to an embodiment of the present invention.
Figure 3:
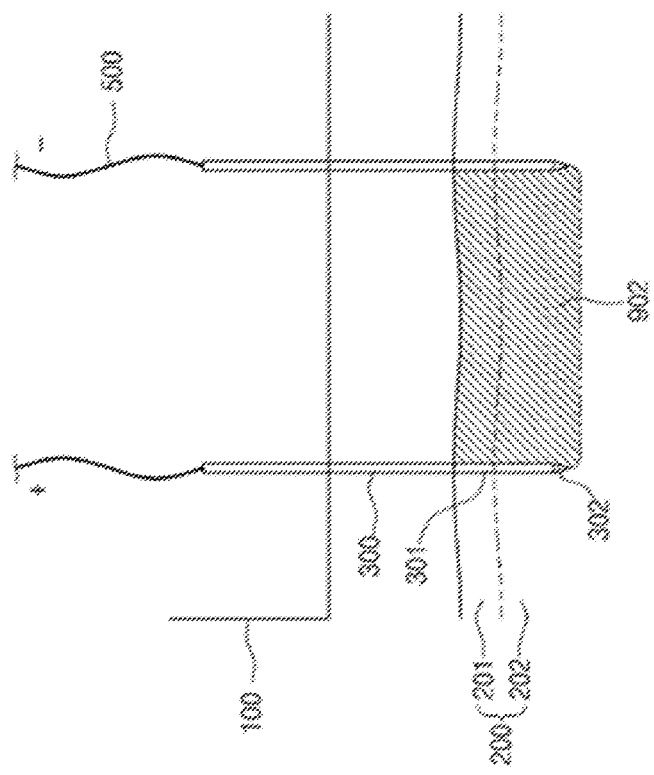
FIG. 3 is a simplified diagram of treatment architecture using non-insulated bipolar needles according to an embodiment of the present invention.
Figure 8:
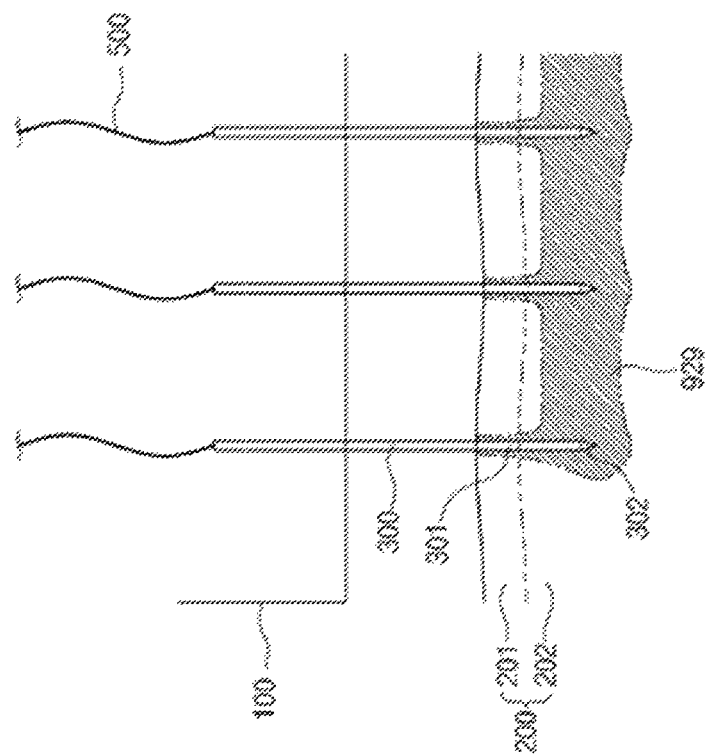
FIG. 8 is a simplified diagram of a treatment architecture according to an embodiment of the present invention.
Figure 7:
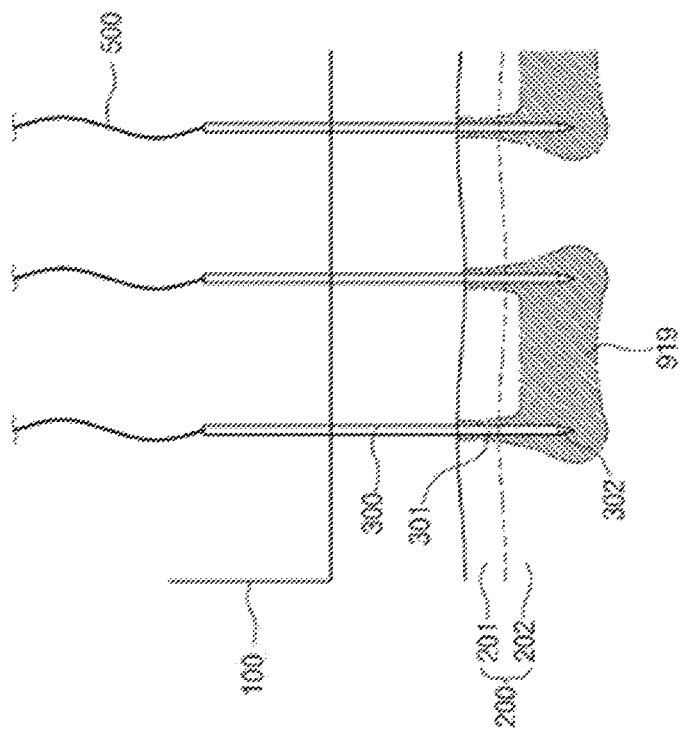
FIG. 7 is a simplified diagram of a treatment architecture according to an embodiment of the present invention.

Some embodiments may employ bipolar needles, AC and high frequency signals. The distance between needles may vary for different embodiments. In an embodiment needles 301 (FIG. 2) may not be located close proximity because if the distance between electrodes or needles is too close, the energy field and the heated area generated by the applied energy field about each needle may be connected or intersect. In another embodiment the energy fields (generating heated areas in dermis) may be expanded and connected in dermis, but not in epidermis as shown in FIGS. 7 and 8.

In an embodiment, alternating current (AC) is the current that changes magnitude and direction periodically and may be a known waveform including a sine wave, triangular, or square wave. AC has characteristics that differ from direct current (DC), which flows in one direction and has a constant polarity. On-grid AC provided by power companies commonly alternates polarity about either at 50 Hz or 60 Hz worldwide.

In an embodiment, actuating needles with AC may be a factor to generate a desired effect or energy field about the each needle. In an embodiment, the AC frequency may be be hundreds of Hz to achieve the desired effect. For high frequency AC sources, the distance between needles may be decreased to compensate for the effect of the high frequency AC source. Low frequency AC sources may affect operation in an embodiment. AC sources having a frequency of 20 Hz or higher may not create a desired operation in an embodiment by controlling other factors. Those control factors are discussed below. In an embodiment, high frequency AC sources may be employed versus low and medium frequencies, and ultrasonic waves or sources.

In an embodiment the AC source may have a frequency above 0.5 MHz and about 2 MHz in another embodiment. Other embodiments may employ an AC signal having a frequency from 0.5 to 10 MHz, 1 to 4 MHz, and 1.5-2.5 MHz where the AC frequency selected range may vary depending on other operating factors that affect desired performance.

During electricity conductivity tests for dry skin and wet skin with AC signals having frequencies of 2 MHz and 1 MHz, it was noted that dry skin had a conductance of about 0.037102 at 2 MHz and about 0.013237 at 1 MHz and wet skin had a conductance of about 0.26649 at 2 MHz and about 0.2214 at 1 MHz. Consequently, RF energy flow or conductance may be smoother or less resistive when applied to wet skin at 2 MHz. Based on the lower conductance the probability for sparking for energy applied at 1 MHz (ignoring other variables) may be three times higher than 2 MHz energy.

In an embodiment a high frequency applied current may create an energy field closer to an electrode or needle than an equivalent energy low frequency current.

For example, when AC signals having a frequency below 0.5 MHz are applied to a needle or electrode the area impacted by the resultant, broad energy field may cause scaring in adjacent epidermis due to overheating regardless of electrode or needle spacing. Accordingly, for areas where a precise treatment is required such as around eyelid, the source frequency may be selected to prevent a broad energy field formation about the needles or electrodes to prevent a harmful impact on an eye. It is noted that when the source energy frequency is 10 MHz or above, the energy field formed about the needles or electrodes may be too narrow and thereby increase treatment time to achieve a desired therapy In various embodiments, achieving a desired therapy may be related to the distance between deployed needles. For example, as the distance between needles decreases the source frequency value may be increased and conversely, as the distance between needles increases, the source frequency value may be decreased to achieve or limit the energy field formation about energized needles or electrodes. In an embodiment, adjacent needles are spaced about 2 mm apart when the needle energizing signal has a frequency of about 2 MHz.

Figure 9B:
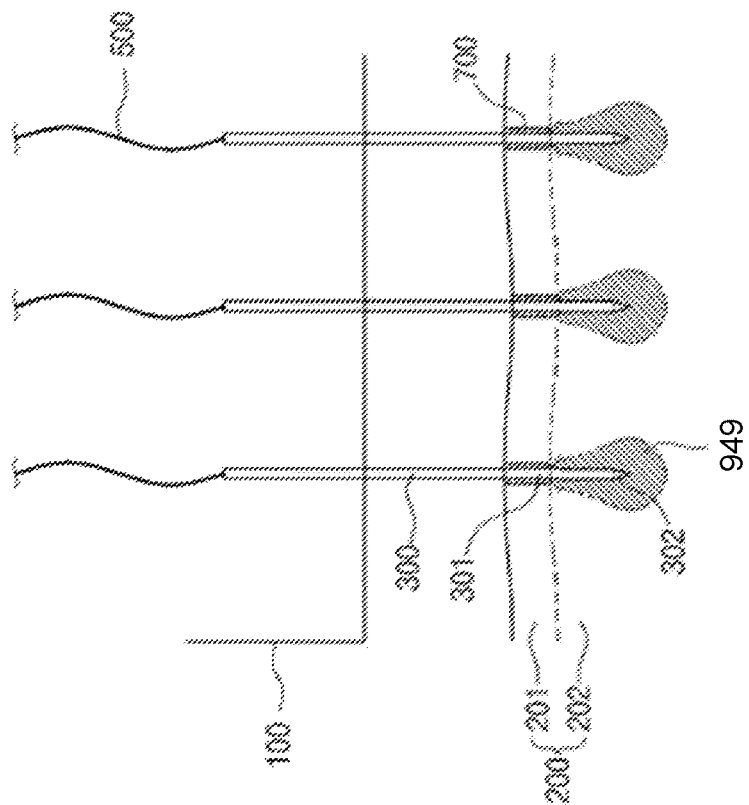
FIG. 9B is a simplified diagram of a treatment architecture according to an embodiment of the present invention with non-overlapping or non-intersecting energy fields.
Figure 9A:
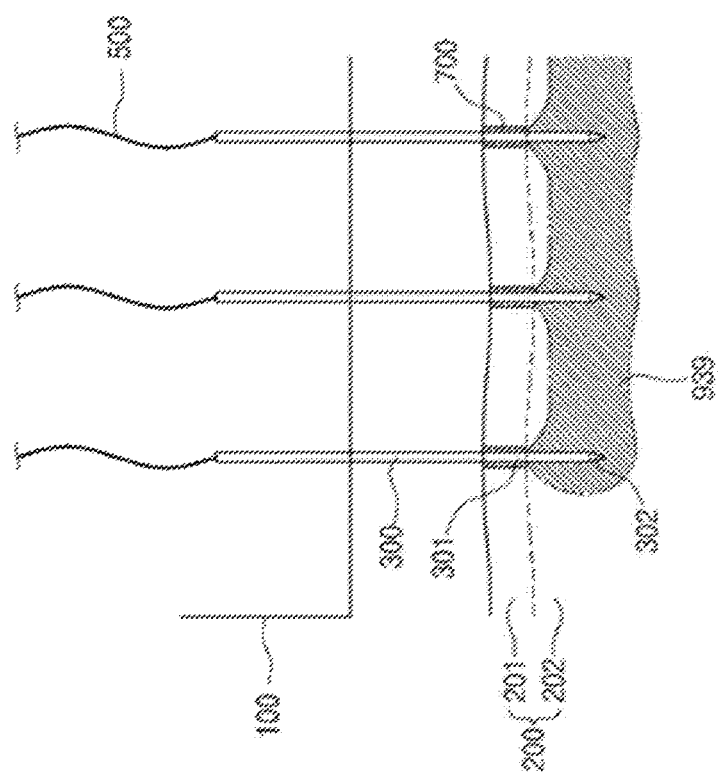
FIG. 9A is a simplified diagram of a treatment architecture according to an embodiment of the present invention with overlapping or intersecting energy fields.

In an embodiment, energized needles may be completely electrically insulated, un-insulated, and only insulated near its tip. Needle insulation may not be necessary fin an embodiment to achieve a desired energy field about the needle, in particular so the temperature is raised about the needle tip and the energy field forms an oval or tear shape in the adjacent dermis while the temperature is minimally raised in the epidermis, as shown in FIGS. 5, 7, 8 and 9B. However, non-electrical insulation coating may not affect energy field formation in about embodiment as shown in FIG. 9B. In an embodiment, needles may be plated with other precious metals or heat-treated to modify needle or electrode conductivity and hardness.

In an embodiment, the needles may not be insulated. In embodiments where at least a portion of the needle is insulated, the segment or area of needle that is configured to contact the dermis may not be insulated. In an embodiment, the entire needle to be energized may be insulated while generating a desired energy field about the needle in the dermis. In an embodiment, a monopole needle insulated except for its tip may be employed to achieve an energy field with a desired shape and temperature. It is important to note that the similarity in energy field shape may have a different effect depending the method applied.

Figure 6:
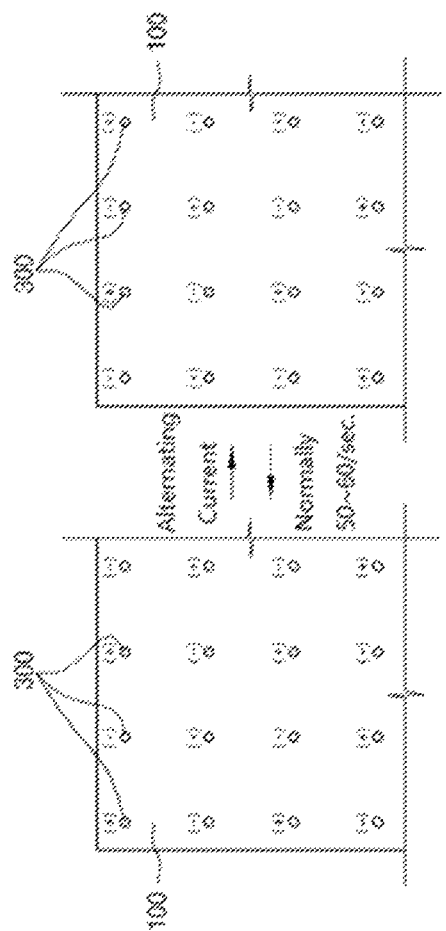
FIG. 6 is a simplified diagram of a treatment architecture illustrating a polarity change of needles according to according to an embodiment of the present invention.
Figure 5:
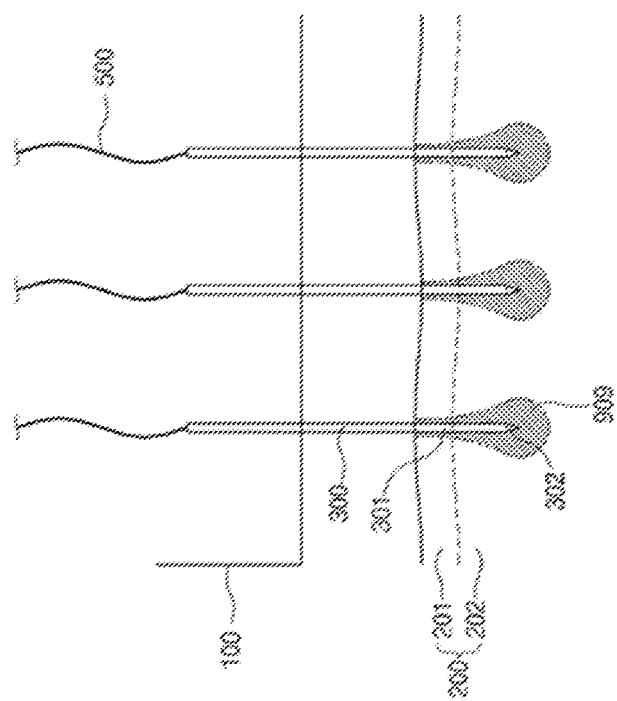
FIG. 5 is a simplified diagram of treatment architecture using non insulated needles according to an embodiment of the present invention.

In an embodiment, different needle arrangements may be employed. In one embodiment, neighboring or adjacent needles 300 may be configured to have opposite polarities as shown in FIG. 6. As shown in FIG. 6, a needle configuration 100 may include needles 300 arranged in a rectangular shape where needles on each corner are configured to have a polarity opposite its adjacent or neighboring needles. In an embodiment, different AC signals having opposite polarities may be applied to needles 300 designated (+) and (−). Because of AC signal characteristics, the polarity of each needle may change many times per second (up to 10 MhZ in an embodiment) and cause a needle 300 polarity to change as shown in FIG. 6 at applied AC signal rate. In an embodiment, each needle is configured to have a polarity that is opposite to its closest neighboring needles, polarity shown as in (+) and (−) in FIG. 6 due to the signals applied to the needles 300 via the RF signal generator 14 (FIG. 1).

Figure 11:
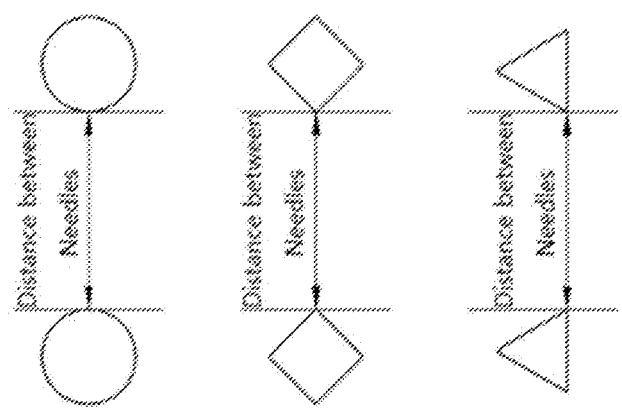
FIG. 11 is a simplified diagram illustrating the distance between two needles according to various embodiments of the present invention.

In an embodiment, a needle 300 cross-section may be configured in a square shape 100 (see FIG. 11). In other embodiments, the needles 300 may be configured in the shape of a rhombus, rectangle, circle, oval, or quadrangle (see FIG. 11). In an embodiment, regardless of shape, the neighboring needles may be configured to have opposite polarities when signals are applied by the RF signal generator 14 (FIG. 1).

In an embodiment, one or more needles 100 may be non-conductive, not energized, or physically removed from particular positions and still produce desired energy fields about the needles in the desired anatomy. In an embodiment, each, closest neighboring needles have opposite polarities, crossing in each direction as in (+) and (−), and a form a square shape 100 having sixteen needles 300.

Figure 10:
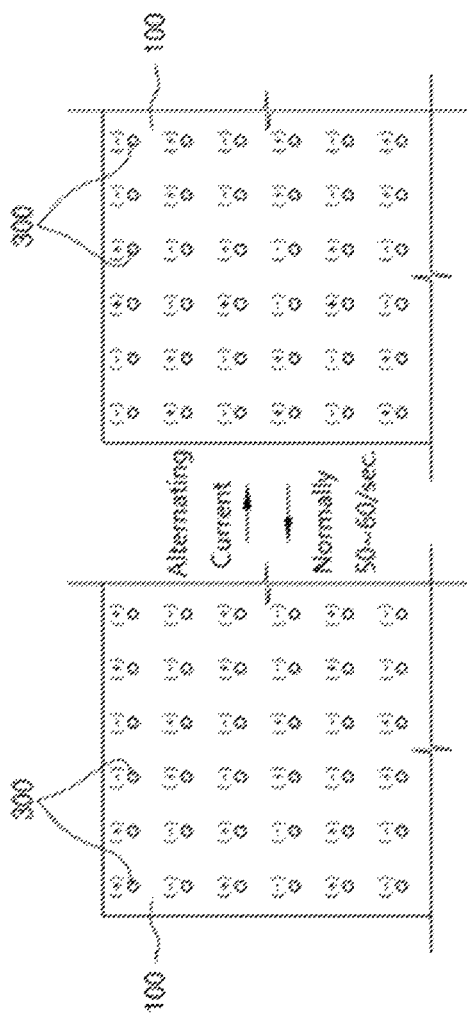
FIG. 10 is a simplified diagram of a treatment architecture illustrating a polarity change of needles according to according to an embodiment of the present invention.

FIG. 10 is a simplified diagram 100 of another needle 300 arrangement 100 according to various embodiments. In an embodiment, the polarity of needles 300 may be configured to change with every two, adjacent needles to form a pattern of (−) (−) (+) (+). In another embodiment, two or more needles may have the same polarity and then next set has an opposite polarity based on the signals applied to the needles 300. A variety of needle 300 polarity combinations, placements, and needle shapes 100 may be used in designing a device that generates a desired energy field about a needle 300 including the configurations shown in FIG. 6 and FIG. 10.

In an embodiment, a device or needle configuration 100 may have a minimum number of needles is 4. In another embodiment, a device or needle configuration may have a minimum of 9 needles with the polarity arrangement shown in FIG. 6 or FIG. 10.

As noted above other needle arrangements can be configured according to various embodiments where the needles produce a desired energy field about the needle.

In order to generate a desired energy field 909 (FIG. 5), 949 (FIG. 9B) about one or more needle 300 tips 302, an embodiment of the present invention may regulate voltage to be applied to a needle in addition to polarity, pattern, shape, adjacent distance, and frequency. In an embodiment, the voltage level applied to one or more needles 300 may determine or be a factor in setting the distance between needles 300 and ensuring safety of a device including the needles 300. In an embodiment, the voltage applied to skin may be measured.

In an embodiment the meaning of "the applied voltage to skin" may be the actual voltage applied to skin between the surface of a needle and the skin the needle contacts. The actual voltage value as applied to the skin may vary on device resistance, needle resistance and skin resistance at different needle positions. The voltage applied to a needle may be different to the voltage actually applied to the skin due to the skin resistance.

Skin resistance values may vary sub-dermally, but negligibly. It is noted that the applied voltage may be directly related to the amount of energy created at a needle. In an embodiment, the voltage applied to a needle or electrode may not exceed 100V with a recommended operating range between 10 to 60V and about 20 to 40V in a particular embodiment. In an embodiment, voltages above 100V may be applied, but there may cause skin overheating or burning so such voltages may not be recommended for use as the operating voltage for skin treatment. The actual skin voltage and the device operating voltage may be controlled by in an embodiment of the present invention. Given a relatively constant skin resistance, controlling the voltage applied to a needle 300 or group of needles 100 may also control the current flowing in the needle and the skin adjacent to the needle. In particular, the electric current may vary depending on voltage and resistance, but it is possible to compute the value of the electric current when device resistance, needle resistance, and skin resistance values are determined based on the equation:

$$V = I * R$$

A systems resistance may be related to device resistance 100, needle resistance 300, and skin 200 resistance in an embodiment.

In order to generate a desired energy field 909, 949 about one or more needle 300 tips 302, an embodiment of the present invention may regulate the energy duty cycle. In an embodiment a system 100 may take a minimum of 0.02 seconds for high frequency energy to reach its stability so a desired energy field 909, 949 is achieved about a needle 302. If the energy duration or cycle is less than 0.02 seconds, a desired energy field 909, 949 may not be achieved in an embodiment. In an embodiment, the minimum duty cycle was set to be 0.5 seconds or greater. A major advantage of this embodiment is the relatively short energy retention or duty cycle with a longest retention time about 0.8 seconds. In another embodiment the energy retention time or duty cycle may be increased by increasing the distance between needles 300 and lowering the applied voltage. In an embodiment the energy retention time or duty cycle is between 0.05 to 0.8 seconds.

An optimal duty cycle, on time, or retention time or delay between cycles is not intuitive given it is relatively short. In an embodiment an acceptable energy delivery delay may be between 0.1 to 0.4 seconds, with a range from 0.1 to 0.2 seconds in another embodiment. It was discovered that using high frequency and low voltage signals applied to needles 300 having a desired spacing created an energy field that enables effective skin treatment. In an embodiment a desirable delay time may be between 0.1-0.4 seconds and as about 0.1-0.2 seconds in a particular embodiment. Determining the parameters to enable the desired energy field according the present invention required countless trials and errors with insight. After developing the embodiments to form the desired energy field, it is possible to use a short load time in conjunction with a high frequency, low voltage, and alternating current signal.

Some existing systems may apply high voltage signals with an on time greater 0.5 seconds to skin via electrodes versus embodiments of the present invention that generate signals having a shorter on time.

In order to generate a desired energy field 909, 949 about one or more needle 300 tips 302, an embodiment of the present invention may employ needles with particular lengths and thicknesses. Needle thickness may vary with needle distance in an embodiment. In an embodiment a needle should be thick enough and made of a material strong enough to withstand repetitive penetrations into a body region, skin in an embodiment. An embodiment may need to balance thickness with possible patient pain and scars.

In an embodiment, a needle may have a diameter or outer profile of about 0.25 mm and 0.30 mm but is not critical to achieve desired energy fields 909, 949. The needle length may also vary depending on the thickness of the body region (skin in embodiment) to be treated and the type of treatment. In general, epidermis depth may be between 0.2 mm and 1 mm and dermis depth may be between 1 mm and 4 mm (from the skin boundary). In an embodiment a needle may configured to reach at least the top of the dermis, at least 0.2 mm in length in an embodiment and have a maximum length of about 5 mm to reach or penetrate to the dermis center or bottom. To ensure safe use in an embodiment a needle length may enable an ideal treatment depth from 1 mm-5 mm. In an embodiment, a needle total length may vary on the device 100, with a range between 1 mm to 4 mm.

Epidermis consists of stratum corneum, stratum granulosum, stratum spinosum, stratum basale, each with a potentially different resistance level. Epidermis may be treated with a device 100 having needles 300 with a length of about 1 mm. Another device 100 according to various embodiments may employ needles have a length of about 6 mm to treat skin's subcutaneous layer. Accordingly in an embodiment a device 100 may employ a needle that penetrates to a depth between 1 mm to 6 mm.

In order to generate a desired energy field 909, 949 about one or more needle 300 tips 302, an embodiment of the present invention may employ needles having a desired distance and shape including the shapes shown in FIG. 11. In an embodiment, the minimum distance between adjacent needles may be about 1.3 mm. In another embodiment, the distance between adjacent needles may be between 1.3-3.0 mm where the needle signal current or needle resistance may be varied based on needle distance while enabling a desired energy field to be formed about the needles.

In an embodiment where the distance between closest neighboring needles is shorter than 1.3 mm, there may be a risk of overheating or scaring. In an embodiment, where the distance between adjacent needles is greater than 3.0 mm, needle activation times may increases in order to achieve the same desired results as the treatment efficiency may decrease significantly. It is noted that the distance between adjacent needles may vary as function of the multiple variables discussed above.

In an embodiment other device operation factors that may vary as a function of the distance between needles including energy level (current, voltage), and a needle's thickness (outer diameter). For example, as the applied energy increases, the needle thickness may increases, the distance between adjacent needles may also be expanded to achieve a desired energy field about the needle(s). It is noted that applied energy is equal to voltage (V) multiplied by current (I) and time (t) (V*I*t).

In another embodiment the distance between adjacent needles may be reduced when the system resistance, AC frequency rate, high frequency rate, and needle length or needle depth increases in any combination. In an embodiment, the distance between adjacent needles may be determined as follows:

$$\text{Distance}=N*(\text{Power}=\text{energy})*(\text{Needle Thickness})* \\ (\text{Conductivity})/(\text{Resistance})*(\text{AC Frequency})* \\ (\text{High Frequency})*(\text{Penetrated Needle Depth})$$

Where:
N: A proportional constant, Resistance: Device resistance, needle resistance, skin resistance $$\text{Energy (Joule)}=W*t \ (W=\text{Watt}, t=\text{time})$$

$$\text{Energy (Joule)}=V*I*t(W=V*I)$$

$$\text{Energy (Joule)}=I^2*R*t(V=I*R)$$

Substituting Energy for V*I*t, the distance between adjacent needles may be determined as follows:

$$\text{Distance}=N*V*I*t*(\text{Needle Thickness})*(\text{Conductivity})/(\text{Resistance})*(\text{AC Frequency})*(\text{High Frequency})*(\text{Penetrated Needle Depth})$$

Other distance calculations are possible according to various embodiments. In an embodiment, a device's 100 needles 300 may fixed (distance between adjacent needles) but may move freely axially to enable movement within a confined space of the device 100.

What is claimed is:
1. A mammalian body treatment apparatus, comprising:
a plurality of electrodes, the nearest electrodes having opposite polarities and the electrodes configured to be deployable into a body segment to be treated; and
a radio frequency (RF) generation module, the RF generation module electrically coupled to the plurality of electrodes and configured to provide an RF signal with oscillating current to the plurality of electrodes that causes energy to be substantially applied to body segments around each electrode.

2. The mammalian body treatment apparatus of claim 1, wherein the RF generation module is configured to provide an RF signal to the plurality of electrodes for a predetermined time interval.

3. The mammalian body treatment apparatus of claim 1, further comprising a drive module to controllably move the plurality of electrodes into a body segment to be treated and a user interface to enable a user to select the depths that the drive module controllably moves the plurality of electrodes into a body segment to be treated.

4. The mammalian body treatment apparatus of claim 1, wherein the electrodes are bipolar.

5. The mammalian body treatment apparatus of claim 1, wherein the plurality of electrodes is arranged into a plurality of rows and columns and neighboring electrodes in each of the plurality of rows columns have opposite polarities.

6. The mammalian body treatment apparatus of claim 1, wherein the plurality of electrodes forms a square configuration.

7. The mammalian body treatment apparatus of claim 1, wherein the plurality of electrodes forms a rectangular configuration and their respective polarities form a checkboard pattern.

8. The mammalian body treatment apparatus of claim 1, wherein the plurality of electrodes are non-insulated.

9. The mammalian body treatment apparatus of claim 1, wherein each electrode of the plurality of electrodes is insulated except at its tip.

10. A method of treating a mammalian body, comprising:
deploying a plurality of electrodes into a body segment to be treated, the nearest electrodes having opposite polarities; and
applying an RF signal with oscillating current to the plurality of electrodes to cause energy to be substantially applied to body segments around each electrode.

11. The method of treating a mammalian body of claim 10, including applying an RF signal to the plurality of electrodes for a predetermined time interval.

12. The method of treating a mammalian body of claim 10, including employing a drive module to controllably move the plurality of electrodes into a body segment to be treated and employing a user interface to enable a user to select the depths that the drive module controllably moves the plurality of electrodes into a body segment to be treated.

13. The method of treating a mammalian body of claim 10, wherein the electrodes are bipolar.

14. The method of treating a mammalian body of claim 10, wherein the plurality of electrodes is arranged into a plurality of rows and columns and neighboring electrodes in each of the plurality of rows columns have opposite polarities.

15. The method of treating a mammalian body of claim 10, wherein the plurality of electrodes forms a square configuration.

16. The method of treating a mammalian body of claim 10, wherein the plurality of electrodes forms a rectangular configuration and their respective polarities form a checkboard pattern.

17. The method of treating a mammalian body of claim 10, wherein the plurality of electrodes are non-insulated.

18. The method of treating a mammalian body of claim 10, wherein each electrode of the plurality of electrodes is insulated except at its tip.

* * * * *